(12) United States Patent
Romiti et al.

(10) Patent No.: US 7,732,640 B2
(45) Date of Patent: Jun. 8, 2010

(54) PROCESS FOR UREA PRODUCTION FROM AMMONIA AND CARBON DIOXIDE

(75) Inventors: Domenico Romiti, Lugano (CH); Paolo Sticchi, Massagno (CH)

(73) Assignee: Urea Casale S.A. (CH)

( * ) Notice: Subject to any disclaimer, the term of this patent is extended or adjusted under 35 U.S.C. 154(b) by 789 days.

(21) Appl. No.: 11/572,387

(22) PCT Filed: Jul. 22, 2005

(86) PCT No.: PCT/EP2005/008033

§ 371 (c)(1),
(2), (4) Date: Jan. 19, 2007

(87) PCT Pub. No.: WO2006/015709

PCT Pub. Date: Feb. 16, 2006

(65) Prior Publication Data

US 2007/0287863 A1 Dec. 13, 2007

(30) Foreign Application Priority Data

Aug. 10, 2004 (EP) .................................. 04018981

(51) Int. Cl.
*C07C 237/04* (2006.01)
*C07C 273/08* (2006.01)
*C07C 273/10* (2006.01)
*C07C 273/16* (2006.01)

(52) U.S. Cl. ............................. 564/66; 564/67; 564/68; 564/69; 564/70; 564/71; 564/72; 564/73

(58) Field of Classification Search ................... 564/66, 564/67, 68, 69, 70, 71, 72, 73
See application file for complete search history.

(56) References Cited

FOREIGN PATENT DOCUMENTS

| EP | 1 188 710 A2 | 3/2002 |
|---|---|---|
| GB | 2 051 757 A | 1/1981 |
| WO | WO 02/090250 A1 | 11/2002 |

*Primary Examiner*—Peter G O'Sullivan
(74) *Attorney, Agent, or Firm*—Akerman Senterfitt

(57) ABSTRACT

A process for urea production comprises a first process step in which ammonia (7) and carbon dioxide (6) are obtained, subjecting natural gas (1) to reforming treatments (12, 14), and a second step of urea (8*a*) production from such ammonia (7) and from carbon dioxide, through a formation of a solution comprising urea and ammonium carbamate in a urea synthesis reactor (20) and a subsequent decomposition of the ammonium carbamate and. urea recovery, the process comprises the steps of:—treating combustion smokes (5) comprising carbon dioxide with an aqueous solution (9*a*) comprising a part (7*b*) of such ammonia (7), obtaining an aqueous ammonium carbamate solution (9*c*);—supplying the solution (9*c*) thus obtained to the second process step.

7 Claims, 1 Drawing Sheet

PROCESS FOR UREA PRODUCTION FROM AMMONIA AND CARBON DIOXIDE

FIELD OF APPLICATION

The present invention refers, in its most general aspect, to a process for urea production from ammonia and carbon dioxide.

In particular this invention refers to a process for urea production of the type in which the ammonia and the carbon dioxide necessary for the urea synthesis are obtained in the same ambit, in the same processing line, in the same industrial area or in the same plant that produces said urea.

More specifically, the present invention concerns a process of the type considered above, comprising a first step in which ammonia and carbon dioxide are produced by subjecting natural gas to a steam reforming treatment, and a second step of urea production from said ammonia and carbon dioxide, through respective steps of formation of a solution of urea and ammonium carbamate in a urea synthesis reactor and of subsequent decomposition of the ammonium carbamate and urea recovery.

PRIOR ART

Processes for urea production from ammonia and carbon dioxide are well known, and it is known that when the urea thus obtained is intended for fertilizer production, there is still a widespread requirement to use natural gas as primary material of the entire production process and, in particular, for the production of ammonia synthesis gases (hydrogen and nitrogen).

It is also known that in the aforementioned processes, the production of synthesis gases is generally carried out at first subjecting the predetermined natural gas to subsequent steam reforming treatments and then separating hydrogen and nitrogen from the carbon dioxide that is obtained with them through the aforementioned treatments. This carbon dioxide itself is used with the ammonia for the urea production.

However, it is well known that, by using natural gas as primary material, the ammonia and the carbon dioxide produced are not in the stechiometric quantities required by the subsequent urea synthesis, but generally there is excess ammonia with respect to CO2. Consequently, to produce urea using all the ammonia produced, it is necessary to have an additional amount of carbon dioxide.

For such a purpose, the prior art teaches to carry out a recovery of pure carbon dioxide actually within the ambit of the same process, in particular from smokes resulting from the burning of natural gas (methane), burnt to provide the necessary heat for the steam reforming treatment of the process natural gas for producing synthesis gases, and discharged by the reforming treatment itself, in which it is contained in significant quantities. In particular, said recovery is carried out by treating (washing) the same combustion smokes with ethanolamines, for example monoethanolamine in aqueous solution (MEA).

Whilst advantageous from various points of view, however, this technique of supplying additional carbon dioxide is complex to be carried out, laborious and not cost-effective. Indeed, it necessarily involves a whole series of chemical reactions variously interconnected and interrelated, which are difficult to carry out and control, which require a plant and relative apparatuses that must be designed for just that purpose, i.e. to recover pure carbon dioxide from the combustion smokes discharged by the reforming step of the natural gas, as well as for the elimination of the discharge products (including oxidized MEA), in considerable quantity, resulting from such a technique.

SUMMARY OF THE INVENTION

The technical problem underlying the present invention is that of devising and providing a process for urea production from natural gas, having characteristics such as to allow the aforementioned drawbacks with reference to the prior art to be overcome.

Such a technical problem is solved, according to the present invention, by a process for urea production comprising a first process step in which ammonia and carbon dioxide are obtained, subjecting natural gas to reforming treatments, and a second step of urea production from said ammonia and from carbon dioxide, through a formation of a solution comprising urea and ammonium carbamate in a urea synthesis reactor and a subsequent decomposition of the ammonium carbamate and urea recovery, characterized in that it comprises the steps of:

treating combustion smokes comprising carbon dioxide with an aqueous solution comprising a part of said ammonia, obtaining an aqueous ammonium carbamate solution;

supplying the solution thus obtained to said second process step.

The characteristics and the advantages of the process according to the invention shall become clearer from the following description of an embodiment thereof, made with reference to the attached drawings, given for indicating and not limiting purposes.

DETAILED DESCRIPTION OF A PREFERRED EMBODIMENT

Figure 1:
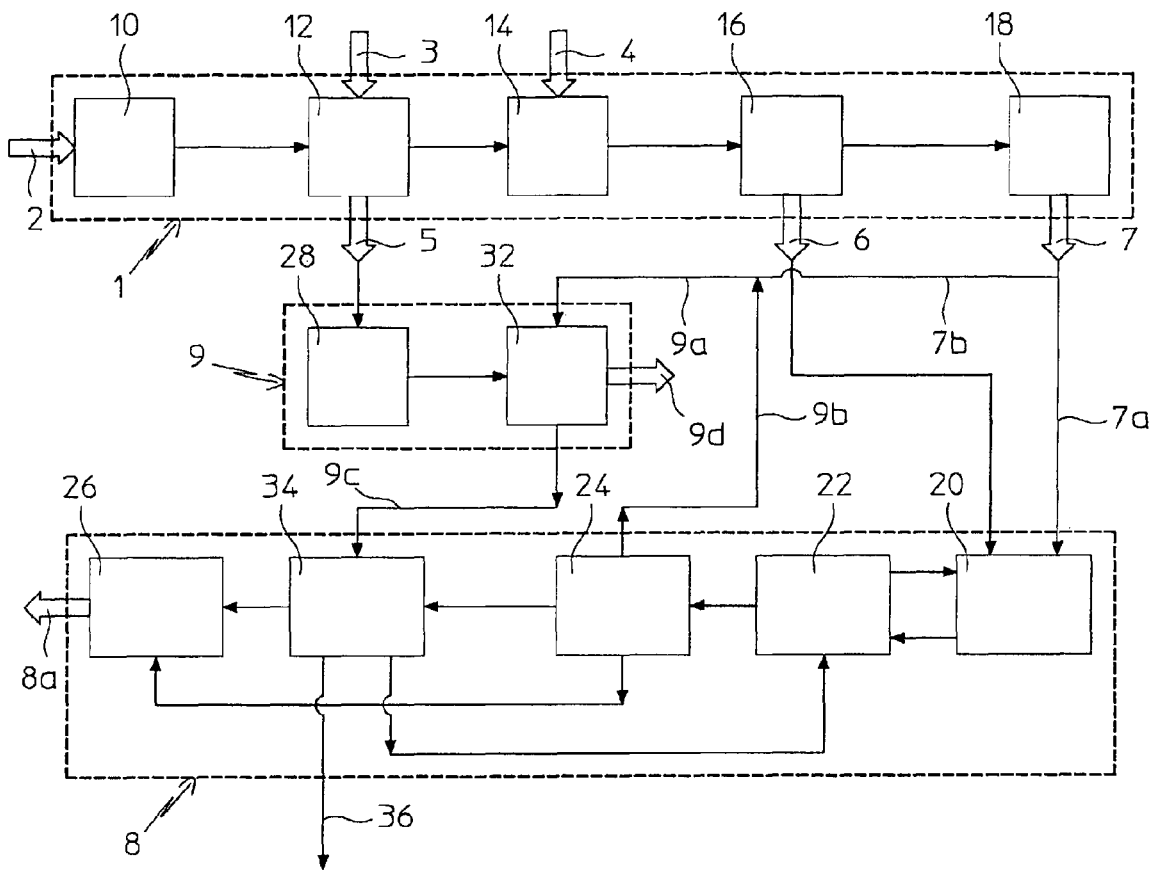
FIG. 1 shows the block diagram of a process for urea production from ammonia, according to the present invention.

With reference to FIG. 1, a process according to the present invention, for urea production, essentially comprises two process steps, variously interconnected, as shall become clear in the rest of the description. A first step in which, from natural gas, ammonia is produced and at the same time substantially pure carbon dioxide is obtained; and a second step in which urea is produced, using the ammonia and the carbon dioxide, generated in said previous first step.

In the first step, carried out in an ammonia plant globally indicated with 1, a natural gas 2, for example methane, after possible desulphurisation in a desulphurisation unit 10, is subjected, in a totally conventional way, to successive catalytic reforming treatments, firstly with steam 3 in a primary reformer 12 and then with air 4 in a secondary reformer 14.

The heat necessary for the primary reforming treatment 12 of the process natural gas is obtained by burning a further flow of natural gas (methane), not represented, thus generating combustion smokes 5 comprising carbon dioxide; whereas a gaseous flow essentially comprising hydrogen, nitrogen and carbon dioxide is discharged from the secondary reformer 14. Hydrogen and nitrogen, freed from the carbon dioxide 6 through a conventional decarbonation treatment in a decarbonation unit 16, for example with MEA, are supplied to a reactor 18, for synthesizing the ammonia 7.

The ammonia 7 and the carbon dioxide 6 at the outlet from the first process step schematically described above, are supplied to the second process step, for the urea production.

It should be remembered that, as known, the ammonia and the carbon dioxide obtained from natural gas in the aforementioned way, are not in the quantitative proportions stechiometrically provided for the urea production, but the ammonia is in excess with respect to the carbon dioxide.

For this reason, in the second process step, carried out in a urea plant globally indicated with 8, only a part 7a of the ammonia and all of the carbon dioxide produced in the first process step, are made to react in a per se known way, in an appropriate synthesis reactor 20, obtaining a solution comprising urea, ammonium carbamate and free ammonia. The ammonium carbamate present in said solution is decomposed and the resulting carbon dioxide and ammonia vapours, together with the free ammonia, are condensed in a decomposition and recovery unit 22 and are recycled to the synthesis reactor 20. The process solution is then subjected to concentration in a concentration unit 24 in which an aqueous solution comprising residual ammonium carbamate is separated from a concentrated urea solution. The concentrated urea solution is then sent, for example, to a granulation stage 26 where solid urea (granules) 8a is obtained, which is then packaged. The aqueous solution resulting from the aforementioned urea concentration treatment in the unit 24 is, on the other hand, sent to a waters treatment unit 34, in which the residual ammonium carbamate still present in the solution is separated and recycled to the synthesis reactor 20 through the decomposition and recovery unit 22, whereas the water thus purified is discharged from the urea plant 8 through the line 36.

In order to use, for the urea production, all of the ammonia 7 produced in the aforementioned first process step, in other words also the ammonia 7b stechiometrically in excess with respect to the carbon dioxide, in accordance with the present invention, preferably said excess ammonia 7b is advantageously used to "recover" the carbon dioxide present in combustion smokes.

Such combustion smokes can be smokes generated for obtaining heat through combustion of natural gas in said first and/or second process step of the process itself, or they can also be generated outside of the industrial area in which the process of the invention is carried out.

In the example of FIG. 1, the combustion smokes 5 generated by the primary reforming treatment of the natural gas are advantageously used. Alternatively, for example, the combustion smokes of boilers present in the plant could be used.

Figure 2:
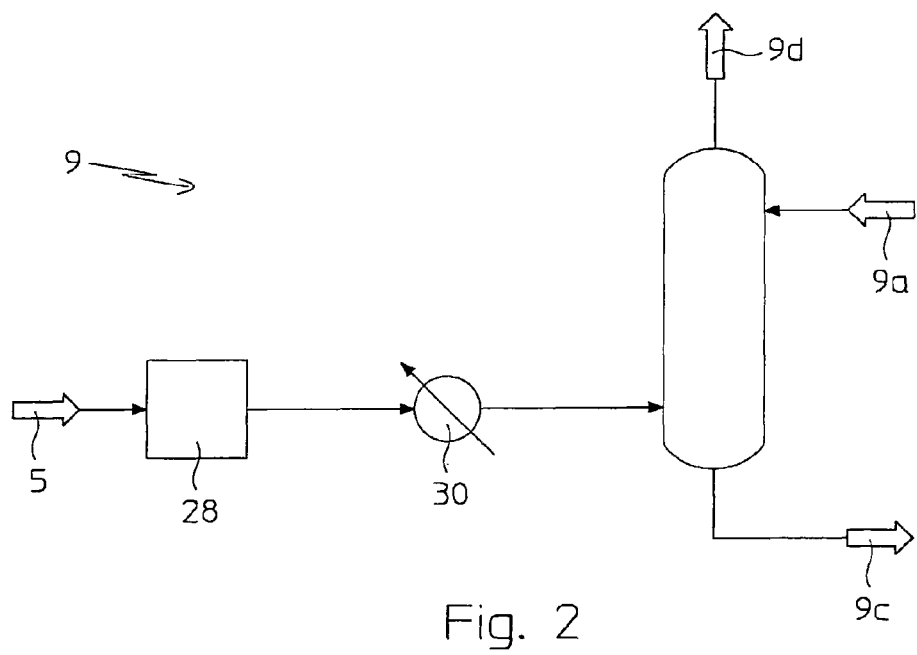
FIG. 2 schematically shows units operating in the process of FIG. 1, according to the present invention.

Advantageously and according to a preferred embodiment of the aforementioned "recovery", carried out in a carbon dioxide recovery section globally indicated with 9 and shown in greater detail in FIG. 2, the combustion smokes 5, purified in a DeNOx purifier 28 (per se known and therefore not described in detail) from the nitrogen oxides possibly contained in them and cooled in a heat exchanger 30, are treated in a washing tower 32 with an aqueous solution 9a of said excess ammonia.

In the example of FIG. 1, the aqueous solution 9a for washing the combustion smokes is obtained by mixing the excess ammonia 7b coming from the ammonia plant 1 with an aqueous ammonium carbamate solution 9b coming from the concentration unit 24 of the urea plant 8 associated with it. Such mixing can take place outside of the washing tower 32 as indicated in FIG. 1, or even inside the tower 32 itself.

In other words, the combustion smokes 5 are washed with such an ammonia solution 9a, in which a large amount of the carbon dioxide comprised in said smokes is absorbed and reacts to form a more concentrated ammonium carbamate aqueous solution 9c.

The smokes 9d, impoverished of carbon dioxide, are then released into the atmosphere in a per se conventional way.

As an alternative to the example of FIG. 1, it is also possible to provide the use of an ammonia solution 9a obtained using a part of ammonia 7 in a smaller amount with respect to said excess 7b, or, in a greater amount than it, for example through the use of an additional amount of ammonia coming from the outside of the ammonia plant 1.

In accordance with another characteristic of the present invention, the ammonium carbamate solution 9c in which the carbon dioxide of the combustion smokes 5 has been absorbed, is supplied to the second process step.

More specifically, the ammonium carbamate solution 9c is advantageously supplied to the urea synthesis reactor 20, preferably following passage through the waters treatment unit 34 and the decomposition and recovery unit 22 together with the ammonium carbamate separated in said waters treatment unit 34. In other words, preferably, the aqueous carbamate solution 9c is combined with the recycled aqueous carbamate solution of the urea plant 8, which follows a path that conventionally passes from the waters treatment unit 34 and from the decomposition and recovery unit 22.

Alternatively, according to a further embodiment of the invention, not represented, the aqueous ammonium carbamate solution 9c is supplied to another part of the urea plant, for example to an additional decomposition unit of the ammonium carbamate (not represented) in which the vapours comprising carbon dioxide and ammonia are then supplied to the synthesis reactor following suitable condensation.

The advantages achieved by the process for urea production fundamentally consist of the fact that all of the ammonia produced in the first step of said process is used for urea production in the second step thereof and the fact that the "recovery" of carbon dioxide from combustion smokes, for example from the smokes discharged from the primary reformer, is easy and cost-effective to carry out, not requiring the complicated operations provided by the prior art.

Moreover, the aforementioned process can be carried out through plants designed ex novo, ensuring the possibility of selecting, without any restriction, the amount of ammonia to be converted into urea, or through existing plants appropriately equipped with a simple new CO2 "recovery" section.

Another advantage of the invention is linked to the fact that in the carbon dioxide recovery section 9 an exothermal carbamate formation reaction develops: the heat freed in such a reaction can thus be used, for example to produce steam.

The finding thus conceived can undergo variants and modifications all of which are covered by the scope of protection of the present invention, as defined by the following claims.

The invention claimed is:

1. Process for urea production from ammonia and carbon dioxide comprising a first process step in which ammonia (7) and carbon dioxide (6) are obtained, subjecting natural gas (1) to reforming treatments (12, 14), and a second step of urea (8a) production from said ammonia (7) and from carbon dioxide, through a formation of a solution comprising urea and ammonium carbamate in a urea synthesis reactor (20) and a subsequent decomposition of said ammonium carbamate and urea recovery, characterized in that it comprises the steps of:

treating combustion smokes (5) comprising carbon dioxide with an aqueous solution (9*a*) comprising a part (7*b*) of said ammonia (7), obtaining an aqueous ammonium carbamate solution (9*c*);

supplying the solution (9*c*) thus obtained to said second process step.

2. Process according to claim 1, characterized in that said aqueous ammonium carbamate solution (9*c*) is supplied to the urea synthesis reactor (20).

3. Process according to claim 1, characterized in that said aqueous ammonium carbamate solution (9*c*) is supplied to the urea synthesis reactor (20) following passage through a waters treatment unit (34) and a decomposition and recovery unit (22) of said second step of urea production.

4. Process according to claim 1, characterized in that said combustion smokes comprising carbon dioxide are treated for a removal of nitrogen oxides possibly contained in them, before said treatment with the aqueous ammonia solution (9*a*).

5. Process according to claim 1, characterized in that said aqueous ammonia solution (9*a*) is obtained by mixing said part (7*b*) of ammonia (7) with an aqueous ammonium carbamate solution (9*b*) coming from a concentration unit (24) of said second step of urea production.

6. Process according to claim 1, characterized in that said combustion smokes (5) are generated by said reforming treatments (12).

7. Process according to claim 1, characterized in that said combustion smokes (5) are produced in said first and/or second process step of the process itself.

\* \* \* \* \*